United States Patent
Li et al.

(10) Patent No.: US 6,696,216 B2
(45) Date of Patent: Feb. 24, 2004

(54) THIOPHENE-CONTAINING PHOTO ACID GENERATORS FOR PHOTOLITHOGRAPHY

(75) Inventors: Wenjie Li, Poughkeepsie, NY (US); Pushkara Rao Varanasi, Poughkeepsie, NY (US); Kuang-Jung Chen, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 09/896,538

(22) Filed: Jun. 29, 2001

(65) Prior Publication Data

US 2003/0008230 A1 Jan. 9, 2003

(51) Int. Cl.$^7$ .............................................. G03F 7/003
(52) U.S. Cl. ..................... 430/270.1; 430/326; 430/921
(58) Field of Search ............................. 430/326, 270.1, 430/914, 921, 922

(56) References Cited

U.S. PATENT DOCUMENTS

| | | | |
|---|---|---|---|
| 3,763,187 A | * 10/1973 | Moyle | |
| 4,024,238 A | * 5/1977 | Riley et al. | |
| 4,087,554 A | * 5/1978 | Haydock et al. | |
| 4,256,828 A | * 3/1981 | Smith | |
| 4,708,925 A | * 11/1987 | Newman | |
| 4,855,017 A | 8/1989 | Douglas | |
| 4,883,740 A | * 11/1989 | Schwalm et al. | 430/270 |
| 5,250,392 A | 10/1993 | Marcotte, Jr. et al. | |
| 5,362,663 A | 11/1994 | Bronner et al. | |
| 5,369,200 A | 11/1994 | Schädeli et al. | |
| 5,374,500 A | * 12/1994 | Carpenter, Jr. et al. | |
| 5,397,680 A | 3/1995 | Schädeli et al. | |
| 5,429,710 A | 7/1995 | Akiba et al. | |
| 5,446,172 A | * 8/1995 | Crivello et al. | |

(List continued on next page.)

FOREIGN PATENT DOCUMENTS

| | | | |
|---|---|---|---|
| DE | 2166953 | * | 1/1977 |
| JP | 7086094 | | 3/1995 |
| JP | 10268522 | | 10/1998 |
| JP | 10274853 | | 10/1998 |

OTHER PUBLICATIONS

Photoacid Generators in Chemically Amplified Resists, Suzuki, Y. et al, SPIE, vol. 3333, Feb. 1998, 735–746.*
JPO English Translation of JP 11–030865, Feb. 1999.*
Srogl, J. et al, J.Am.Chem.Soc. 1997, 119, 12376–12377.*
Chemical Abstract DN 133:309819.*
Chemical Abstract DN 79:66114.*
Chemical Abstract DN 112:7273.*
Chemical Abstract DN 126:277376.*
Chemical Abstract DN 128:47852.*
Chemical Abstract DN 131:184733.*
Chemical Abstract DN 131:116028.*
Chemical Abstract DN 133:252085.*
Chemical Abstract DN 124:29313.*
Chemical Abstract DN 125:167720.*
Chemical Abstract DN 101:230273.*
Chemical Abstract DN 101:130545.*
Chemical Abstract DN 88:169953.*
Chemical Abstract DN 87:84025.*
Chemical Abstract DN 87:58525.*
Chemical Abstract DN 86:115658.*
Margida, A.J. et al., J.Org.Chem.1984, 49 (19), 3643–3646.*
Margida, A.J. et al., J.Org.Chem.1984, 49 (19), 4703–4706.*
Carroll, M.A. et al., Tetrahedron Letters 2000, 41 (28), 5393–5396.*
Kitamura, T. et al., Tetrahedron Letters 1996, 37 (21) 3721–3722.*
Direct Condensation of [Hydroxy(tosyloxy)iodo]arenes with Thiophenes. A Convenient, Mild Synthesis of Aryl(2–thienyl)iodonium Tosylates, Anthony J. Margida and Gerald F. Koser, Dept. of Chemistry, The University of Akron, Akron, Ohio 44325, Mar. 15, 1984, 1984 American Chemical Society3664, J. Org. Chem., vol. 49, No. 19, 1984.
Sulfonium Salts. Participants par Excellence in Metal–Catalyzed Carbon–Carbon Bond–Forming Reactions, Kiri Srogl, Gary D. Allred, and Lanny S. Liebeskind, J. Am. Chem. Soc. 1997, 119, 12376–12377.
Exchange of Carbon Ligands at Iodine in Iodonium Salts. A Direct Synthesis of Aryl(2–furyl)iodonium Tosylates from Aryl(tert–butylethynl)iodonium Tosylates, Anthony J. Margida and Gerald F. Koser, Depart. of Chemistry, The University of Akron, Akron, Ohio 44325, Mar. 06, 1984, Am. Chemical Society.

*Primary Examiner*—Rosemary Ashton
(74) *Attorney, Agent, or Firm*—Scully, Scott, Murphy & Presser; Steven Capella, ESq.

(57) ABSTRACT

Thiophene-containing photo acid generators having either of the following general formulas:

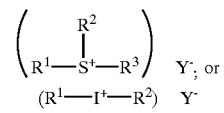

wherein at least one of $R^1$, $R^2$ or $R^3$ is thiophene or thiophene that is substituted with alkyl, alkoxy or cycloalkyl, and the remaining $R^1$, $R^2$ or $R^3$, not containing a thiophene moiety, are independently selected from the group consisting of alkyl, cycloalkyl and aryl, or at least one of $R^1$, $R^2$ or $R^3$ are joined together to form a cyclic moiety having from about 4 to about 8 ring carbon atoms; and Y is a counter ion, are disclosed as well as the use thereof as a component of a chemically amplified resist composition. In addition to the thiophene-containing photo acid generator, the inventive composition includes a chemically amplified base polymer, a solvent, an optional photosensitizer, an optional base, an optional dissolution modifying agent and an optional surfactant.

26 Claims, No Drawings

U.S. PATENT DOCUMENTS

| | | |
|---|---|---|
| 5,562,801 A | 10/1996 | Nulty |
| 5,593,812 A | 1/1997 | Babich et al. |
| 5,618,751 A | 4/1997 | Golden et al. |
| 5,744,376 A | 4/1998 | Chan et al. |
| 5,753,412 A | 5/1998 | Babich et al. |
| 5,770,345 A | 6/1998 | Babich et al. |
| 5,773,194 A * | 6/1998 | Hattori et al. |
| 5,801,094 A | 9/1998 | Yew et al. |
| 5,821,169 A | 10/1998 | Nguyen et al. |
| 6,074,800 A | 6/2000 | Breyta et al. |
| 6,187,504 B1 * | 2/2001 | Suwa et al. ............... 430/270.1 |
| 6,358,665 B1 * | 3/2002 | Pawlowski et al. |
| 6,406,830 B2 * | 6/2002 | Inoue et al. ............. 430/270.1 |
| 6,482,568 B1 * | 11/2002 | Douki et al. ............. 430/270.1 |
| 2002/0045122 A1 * | 4/2002 | Iwasa et al. ............. 430/270.1 |

\* cited by examiner

THIOPHENE-CONTAINING PHOTO ACID GENERATORS FOR PHOTOLITHOGRAPHY

FIELD OF THE INVENTION

The present invention relates to photolithography, and more particularly to thiophene-containing photo acid generators which efficiently generate photo acids when they are exposed to UV light. The present invention is also directed to chemically amplified resist compositions which include the inventive thiophene-containing photo acid generator as one component thereof.

BACKGROUND OF THE INVENTION

In the field of semiconductor manufacturing, optical lithography has been the mainstream approach used in patterning semiconductor devices. In typical prior art lithography processes, UV light is projected onto a silicon wafer coated with a thin layer of photosensitive resist through a mask that defines a particular circuitry pattern. Exposure to UV light, followed by subsequent baking, induces a photochemical reaction which changes the solubility of the exposed regions of the photosensitive resist. Thereafter, an appropriate developer, usually an aqueous base solution, is used to selectively remove resist either in the exposed regions (positive-tone resists) or, in the unexposed regions (negative-tone resists). The pattern thus defined is then imprinted on the silicon wafer by etching away the regions that are not protected by the resist with a dry or wet etch process.

One type of photosensitive resist employed in the prior art is a chemically amplified resist which uses acid catalysis. A typical prior art chemically amplified resist, for example, is formulated by dissolving an acid sensitive polymer and a photo acid generator in a casting solution. A chemically amplified resist is especially useful when relatively short wavelength radiation is employed; including deep UV radiation 150–315 nm wavelengths, and mid-UV radiation, e.g., 350–450 nm wavelengths. The shorter wavelengths are typically desired to increase resolution, and thus, decrease feature size of the semiconductor devices, but fewer photons are radiated for a given energy dose.

Accordingly, higher exposure doses are typically required when using UV radiation to obtain a sufficient photochemical response in the resist unless a chemically amplified resist is employed. In a chemically amplified resist, acid sensitivity of the base polymer exists because acid sensitive side chain groups are bonded to the polymer backbone. When such a resist is exposed to radiation, the photo acid generator produces an acid that, when the resist is heated, causes catalytic cleavage of the acid sensitive side chain groups. A single acid catalyst molecule generated in this manner may be capable of cleaving multiple side chain groups, thus allowing lower exposure doses for the needed photochemical response.

Several acid catalyzed chemically amplified resists have been developed, although their photo acid generators are primarily suited for deep UV radiation, typically at about 248 nm. By comparison, there are very few, if any, photo acid generators which efficiently generate photo acids when they are exposed to a wavelength of light of about 220 nm or less. The challenge for designing photo acid generators for resists exposed at 220 nm involves a balance between absorption, photosensitivity, stability, dissolution and etch resistance.

For 248 nm resists, aryl onium salts (triarylsulfoniums or diaryliodoniums) are typically used as photo acid generators. However, such photo acid generators are generally too absorbing when exposed to wavelengths shorter than 220 nm.

In view of the above-mentioned drawbacks with prior art photo acid generators, there is a need for developing new and improved photo acid generators which can be effectively used with various chemically amplified base polymers at exposure wavelengths of about 220 nm or less.

SUMMARY OF THE INVENTION

One object of the present invention is to provide a new class of photo acid generator that can be employed with various chemically amplified base polymers.

A further object of the present invention is to provide photo acid generators for chemically amplified resists that can used at wavelengths of about 220 nm or less.

Another object of the present invention is to provide a photo acid generator having the proper balance of absorption, photosensitivity, stability, dissolution and etch resistance.

A still further object of the present invention is to provide a photo acid generator that works with 248 nm chemically amplified base polymers, 193 nm chemically amplified base polymers, and 157 nm chemically amplified base polymers.

An even further object of the present invention is to provide a chemically amplified resist composition which has a high resolution at wavelengths of about 220 nm or less.

These and other objects and advantages are achieved in the present invention by using thiophene-containing photo acid generators in place of standard hydrocarbon aromatic ring-containing sulfonium or iodonium photo acid generators. By incorporating thiophene units into sulfonium or iodonium compounds, the absorption of the photo acid generator at low wavelengths (less than about 220 nm) is greatly reduced. Additionally, the thiophene-containing photo acid generators of the present invention still maintain relatively high thermal stability and photosensitivity. Moreover, the chemically amplified resists of the present invention absorb less light at lower wavelengths (220 nm or less) than conventional photo acid generators, which may lead to the inventive chemically amplified resist exhibiting high resolution at these lower wavelengths.

The term "thiophene" as used herein denotes a compound having the following structural formula:

as well as substituted compounds wherein one or more of the ring carbon atoms (not shown) is substituted with a substituent other than hydrogen.

The present invention also provides a chemically amplified resist composition which comprises at least one thiophene-containing photo acid generator having either of the following general formulas:

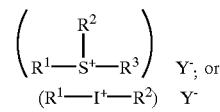

wherein at least one of $R^1$, $R^2$ or $R^3$ is thiophene or thiophene that is substituted with alkyl, alkoxy or cycloalkyl, and the remaining $R^1$, $R^2$ or $R^3$, not containing a thiophene moiety, are independently selected from the group consisting of alkyl, cycloalkyl and aryl, or at least one of $R^1$, $R^2$ or $R^3$ are joined together to form a cyclic moiety having from about 4 to about 8 ring carbon atoms; and Y is a counter ion such as a halogen, perfluorinated alkyl sulfonate, perfluorinated aryl sulfonate, perfluorinated alkyl sulfonyl methide, perfluorinated alkyl sulfonyl imide, perfluorinated aryl sulfonyl methide, perfluorinated aryl sulfonyl imide and the like thereof. Preferred counter ions are perfluorinated alkyl compounds.

In addition to thiophene-containing photo acid generators, the inventive chemically amplified resist composition also includes a chemically amplified base polymer and a solvent as essential components. Optional components that may also be present in the inventive chemically amplified resist composition include: a photosensitizer that is capable of absorbing irradiation in the mid-UV, deep-UV, extreme-UV, X-ray or e-beam range; a base; a dissolution modifying agent (DMA) and/or a surfactant.

DETAILED DESCRIPTION OF THE INVENTION

As stated above, the present invention is directed to novel thiophene-containing photo acid generators which efficiently generate photo acids when they are exposed to UV light. The novel photo acid generators of the present invention have a proper balance between absorption, photosensitivity, stability, dissolution and etch resistance thus making them a viable candidate for replacing conventional aryl onium and aryl sulfonium salts. The inventive thiophene-containing photo acid generators of the present invention do not absorb much light, therefore the inventive photo acid generators are especially suitable for use when they are exposed to wavelengths of 220 nm or less, which could, in turn, equate to better resolutions at these wavelengths.

The thiophene-containing photo acid generators of the present invention are formulated with a chemically amplified base polymer and a solvent so as to make the inventive chemically amplified resist composition which is applied onto a substrate needing patterning (e.g., a semiconductor chip or wafer) using a conventional deposition process such as spin-on coating which is well known in the art. Following deposition, a conventional baking step may be employed to drive-off any residual solvent remaining in the system. Next, the chemically amplified resist is subjected to a conventional patterning process which includes exposure to a pattern of radiation and developing the pattern using an appropriate developer solution.

The chemically amplified resist composition of the present invention includes at least one chemically amplified base polymer, at least one thiophene-containing photo acid generator of the present invention and a solvent including a solvent system. Each of the aforementioned components of the inventive chemically amplified resist composition will now be described in greater detail.

The chemically amplified base polymer employed in the present invention includes any acid sensitive polymer that is capable of undergoing chemical transformations upon exposure to UV light which alters the solubility of the polymer in either the exposed regions or the unexposed regions. That is, the base polymers employed in the present invention include any acid sensitive polymer having acid sensitive side chains which can undergo catalytic cleavage in the presence of an acid generated by the inventive thiophene-containing photo acid generator.

The base polymer resin of the present invention may be either a positive-tone base polymer resin or a negative tone-base polymer resin. In such polymers, the acid sensitivity exists because of the presence of acid sensitive side chains that are bonded to the polymer backbone. Such acid sensitive base polymers including acid sensitive side chains are conventional and are well known in the art.

For example, the present invention contemplates the use of 248 nm base polymers such as phenolic-containing resins, e.g., poly(hydroxystyrene) polymers; 193 nm base polymers such as poly(meth)acrylates; copolymers of cyclic olefins and maleic anhydride; cyclic olefin addition polymers; cyclic olefin-maleic anhydride-(meth)acrylate hybrid polymers and cyclic olefin-(meth)acrylate polymers; as well as 157 nm base polymers such as fluorine-and/or silicon-containing polymers. In addition to the above-mentioned acid sensitive polymers, the present invention also includes phenol formaldehydes, acrylamides, imides or hydroxyimide group type polymers.

Of the chemically amplified base polymers mentioned hereinabove, it is particularly preferred to use 193 and 157 nm base polymers. In a highly preferred embodiment of the present invention, the chemically amplified base polymer is a 193 nm polymer such as a cyclic olefin addition polymer or a cyclic olefin-maleic anhydride copolymer.

In some embodiments of the present invention, the acid sensitive side chains of the acid sensitive polymers are protected with various acid labile protecting groups that are well known to those skilled in the art. For example, the acid sensitive side chains may be protected with high activation energy protecting groups such as t-butyl ester or t-butyl carbonyl groups, a low activation energy protecting group such as acetal, ketal, or silyethers, or a combination of both low and high activation energy protecting groups may also be used.

The chemically amplified base polymers employed in the present invention are prepared utilizing conventional techniques well known in the art. These include liquid or gas phase polymerizations or copolymerizations using cationic, anionic or free-radical catalysts or Zieglar-Natta catalysts.

Another required component of the inventive chemically amplified resist composition is a thiophene-containing photo acid generator which has one of the following formulas:

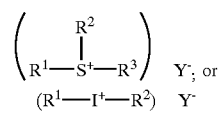

wherein at least one of $R^1$, $R^2$ or $R^3$ is thiophene or thiophene that is substituted with alkyl, alkoxy, or cycloalkyl, and the remaining $R^1$, $R^2$ or $R^3$, not containing a thiophene moiety, are independently selected from the group consisting of alkyl, cycloalkyl and aryl, or at least one of $R^1$, $R^2$ or $R^3$ are joined together to form a cyclic moiety having from about 4 to about 8 ring carbon atoms; and Y is a counter ion including, but not limited to: halogen, perfluorinated alkyl sulfonate, perfluorinated aryl sulfonate, perfluorinated alkyl sulfonyl methide, perfluorinated alkyl sulfonyl imide, perfluorinated aryl sulfonyl methide, or perfluorinated aryl sulfonyl imide. Highly preferred counter ions are the perfluorinated alkyl compounds mentioned above.

Note that the thiophene-containing photo acid generators of the present invention are compounds which generate an acid upon exposure to energy. The photo acid generators are commonly employed herein to induce the chemical transformation of the acid sensitive base polymer, and they are particularly suitable for use when low wavelength exposure (220 nm or less) lithographic processes are employed.

The term "alkyl" as used herein denotes a straight chain or branched aliphatic hydrocabon which includes from about 1 to about 10 carbon atoms. Illustrative examples of suitable alkyls that can be employed in the present invention include: methyl, ethyl, propyl, isopropyl, t-butyl, butyl, pentyl, hexyl, heptyl and the like.

The term "alkoxy" as used herein denotes a group having the formula —OR wherein R is alkyl as defined above. Illustrative examples include: methoxy, ethoxy, and propoxy.

The term "cycloalkyl" denotes a cyclic group which contains from about 3 to about 12 ring aliphatic carbon atoms which may be substituted or unsubstituted. Illustrative examples of such cycloalkyls include: cyclopropane, cyclobutane, cyclopentane, 1-ethyl-3-methylcyclopentane, methylcyclopentane and the like.

The term "aryl" includes aromatic hydrocarbons having from about 3 to about 12 carbon atoms. Illustrative examples of some aryls include: phenyl, naphthyl and the like.

Illustrative examples of some preferred thiophene-containing photo acid generators which satisfy one of the above formulas and thus can be employed in the present invention include, but are not limited to: dimethyl (2-thienyl) sulfonium perfluorinated alkyl sulfonate, diphenyl-2-thienyl sulfonium perfluorinated alkyl sulfonate, and, 2-thienyl-tetrahydrothiophenium perfluorinated alkyl sulfonate. Of these thiophene-containing photo acid generators, it is highly preferred to employ dimethyl (2-thienyl) sulfonium perfluorinated alkyl sulfonate as the photo acid generator in the inventive chemically amplified resist composition.

The thiophene-containing photo acid generators are made using conventional synthesis methods well known to those skilled in the art. For example, the thiophene-containing photo acid generators may be made by reacting a thiophene-containing sulfide with an alkyl halide in the presence of silver sulfonate.

Another required component of the inventive chemically amplified resist composition is a solvent which is capable of dissolving the acid sensitive polymer. Illustrative examples of such solvents include, but are not limited to: ethers, glycol ethers, aromatic hydrocarbons, ketones, esters and the like. A solvent system including a mixture of the aforementioned solvents is also contemplated herein.

Suitable glycol ethers that can be employed in the present invention include: 2-methoxyethyl ether (diglyme), ethylene glycol monomethyl ether, propylene glycol monomethyl ether, propylene glycol monomethylether acetate (PGMEA) and the like.

Illustrative examples of suitable aromatic hydrocarbon solvents that may be employed in the present invention include: toluene, xylene, and benzene. Examples of ketones include: methylisobutylketone, 2-heptanone, cycloheptanone, and cyclohexanone. An example of an ether solvent is tetrahydrofuran, whereas ethyl lactate and ethoxy ethyl propionate are examples of ester solvents that may be employed herein.

Of the various solvents mentioned above, it is preferred that a glycol ether such as PGMEA be employed in the present invention.

In addition to the above required components, the inventive chemically amplified resist composition may also include at least one photosensitizer, at least one base, at least one dissolution modifying agent (DMA), at least one surfactant and any combination or mixtures thereof such as a photosensitizer and a base.

The optional photosensitizer is composed of compounds containing chromophores that are capable of absorbing irradiation in the mid-IV, deep-UV, extreme-UV, X-ray or e-beam range. Illustrative examples of such compounds include, but are not limited to: 9-anthracene methanol, coumarins, 9,10-bis(trimethoxysily ethynyl) anthracene and polymers containing these chromophores. Of these compounds, it is highly preferred to use 9-anthracene methanol as the photosensitizer.

The optional bases that can be employed in the present invention include, but are not limited to: berberine, cetyltrimethylammonium hydroxide, 1,8-bis(dimethylamino) naphthalene, tetrabutyl ammonium hydroxide (TBAH), amines, polymeric amines and the like. When a base is employed with the inventive chemically amplified resist composition, it is highly preferred to use TBAH as the base.

The resist compositions of the present invention may optionally contain a dissolution modifying agent (DMA). The DMA additives generally enable and/or enhance the ability to resolve ultrafine lithographic features in response to conventional aqueous alkaline developers. The DMA additives are preferably characterized by the presence of at least one alicyclic moiety. Preferably, the DMA additive contains at least about 10 carbon atoms, more preferably at least 14 carbon atoms, most preferably about 14 to 60 carbon atoms. The DMA additive preferably contains one or more additional moieties such as acid-labile pendant groups which undergo cleaving in the presence of acid to provide a constituent which acts to promote alkaline solubility of the radiation-exposed portions of the resist. Preferred DMA additives are selected from the group consisting of saturated steroid compounds, non-steroidal alicyclic compounds, and non-steroidal multi-alicyclic compounds having plural acid-labile connecting groups between at least two alicyclic moieties. More preferred DMA additives include lithocholates such as t-butyl-3-trifluoroacetyllithocholate, t-butyl adamantine carboxylate, and bis-adamantyl t-butyl carboxylate. Bis-adamantyl t-butyl carboxylate is a most preferred DMA additive. If desired, a combination of DMA additives can be used.

The optional surfactants that can be employed in the present invention include any surfactant that is capable of improving the coating homogeneity of the chemically amplified resist composition of the present invention. Illustrative examples include: fluorine-containing surfactants such as 3M's FC-430® and siloxane-containing surfactants such as Union Carbide's Silwet® series.

In accordance with the present invention, the chemically amplified resist composition of the present invention comprises from about 5 to about 30 weight % chemically amplified base polymer, from about 50 to about 90 weight % solvent, and from about 0.5 to about 10 weight % thiophene-containing photo acid generator (said weight % thiophene-containing photo acid generator being based on the total weight of base polymer present in the composition). When a photosensitizer is employed, it is present in an amount of from about 0.001 to about 8 weight %, based on the total weight of base polymer present in the composition. If a base is employed, the optional base is present in an amount of from about 0.1 to about 1 weight %, based on the total weight of base polymer present in the composition. When a surfactant is employed, it is typically present in amount of from about 0.001 to about 0.1 weight %, based on the total weight of base polymer present in the composition. When a DMA is employed, it is typically present in an amount of from about 5 to about 25 weight %, based on the total weight of base polymer present in the composition.

More preferably, the chemically amplified resist composition of the present invention comprises from about 10 to about 20 weight % of chemically amplified base polymer, from about 80 to about 90 weight % solvent, and from about 1 to about 5 weight % of thiophene-containing photo acid generator, based on the total weight of base polymer present in the composition, optionally, from about 0.01 to about 5 weight % photosensitizer, based on the total weight of base polymer present in the composition, optionally, from about 0.1 to about 0.5 weight % base, based on the total weight of base polymer present in the composition, optionally from about 10 to about 20 weight % DMA, based on the total weight of base polymer present in the composition, and, optionally, from about 0.001 to about 0.01 weight % surfactant, based on the total weight of base polymer present in the composition.

Note that the amounts given above are exemplary and that other amounts of each of the above components, which are typically employed in the photolithography industry, can also be employed herein.

The chemically amplified resist composition of the present invention is made using conventional processing techniques that are typically employed in the art of photolithography. For example, the chemically amplified resist is made by dissolving one of the aforementioned base polymers into an appropriate solvent and thereafter adding one or more of the thiophene-containing photo acid generators of the present invention thereto.

The inventive chemically amplified resist composition is used in providing a desired pattern to a substrate using conventional processes well known in the art. This includes depositing the inventive chemically amplified resist composition onto a substrate needing patterning via spin-on coating or another like technique, optionally heating the deposited chemically amplified resist composition to drive-off any solvent therefrom, exposing the chemically amplified resist to a pattern of radiation, developing the pattern utilizing a conventional developer solution, transferring the pattern from the chemically amplified resist to the underlying substrate by employing a conventional etching process such as reactive-ion etching, and removing the chemically amplified resist using a conventional stripping process well known to those skilled in the art.

Specifically, the resist compositions of the invention (containing the acid generators of the invention) are specially useful for lithographic processes used in the manufacture of integrated circuits on semiconductor substrates. The compositions are especially useful for lithographic processes using 248 nm or 193 nm UV radiation. Where use of other radiation (e.g. mid-UV, x-ray, or e-beam) is desired, the compositions of the invention can be adjusted (if necessary) by the addition of an appropriate dye or sensitizer to the composition. The general use of the resist compositions of the invention in lithography for semiconductors is described below.

Semiconductor lithographic applications generally involve transfer of a pattern to a layer of material on the semiconductor substrate. The material layer of the semiconductor substrate may be a metal conductor layer, a ceramic insulator layer, a semiconductor layer or other material depending on the stage of the manufacture process and the desired material set for the end product. In many instances, an antireflective coating (ARC) is applied over the material layer before application of the resist layer. The ARC layer may be any conventional ARC which is compatible with acid catalyzed resists.

Typically, the solvent-containing resist composition is applied to the desired semiconductor substrate using spin coating or other technique. The substrate with the resist coating is then preferably heated (pre-exposure baked) to remove the solvent and improve the coherence of the resist layer. The thickness of the applied layer is preferably as thin as possible with the provisos that the thickness is preferably substantially uniform and that the resist layer be sufficient to withstand subsequent processing (typically reactive ion etching) to transfer the lithographic pattern to the underlying substrate material layer. The pre-exposure bake step is preferably conducted for about 10 seconds to 15 minutes, more preferably about 15 seconds to one minute. The pre-exposure bake temperature may vary depending on the glass transition temperature of the resist.

After solvent removal, the resist layer is then patternwise-exposed to the desired radiation (e.g., 193 nm ultraviolet radiation). Where scanning particle beams such as electron beam are used, patternwise exposure may be achieved by scanning the beam across the substrate and selectively applying the beam in the desired pattern. More typically, where wavelike radiation forms such as 193 nm ultraviolet radiation are used, the patternwise exposure is conducted through a mask which is placed over the resist layer.

After the desired patternwise exposure, the resist layer is typically baked to further complete the acid-catalyzed reaction and to enhance the contrast of the exposed pattern. The post-exposure bake is preferably conducted at about 100°–175° C., more preferably about 125°–160° C. The post-exposure bake is preferably conducted for about 30 seconds to 5 minutes.

After post-exposure bake, the resist structure with the desired pattern is obtained (developed) preferably by contacting the resist layer with an alkaline solution which selectively dissolves the areas of the resist which were exposed to radiation in the case of positive resist (or unexposed areas in the case of negative resist). Preferred alkaline solutions (developers) are aqueous solutions of tetramethyl ammonium hydroxide. Preferably, the resist compositions of the invention can be developed with conventional 0.26N aqueous alkaline solutions. The resist compositions of the invention can also be developed using 0.14N or 0.21N or other aqueous alkaline solutions. The resulting resist structure on the substrate is then typically dried to remove any remaining developer solvent. The resist compositions of the invention are generally characterized in that the product resist structures have high etch resistance. In some instances, it may be possible to further enhance the etch resistance of the resist structure by using a post-silylation technique using methods known in the art.

The pattern from the resist structure may then be transferred to the material (e.g., ceramic, metal or semiconductor) of the underlying substrate. Typically, the transfer is achieved by reactive ion etching or some other etching technique. In the context of reactive ion etching, the etch resistance of the resist layer is especially important. Thus, the compositions of the invention and resulting resist structures can be used to create patterned material layer structures such as metal wiring lines, holes for contacts or vias, insulation sections (e.g., damascene trenches or shallow trench isolation), trenches for capacitor structures, etc. as might be used in the design of integrated circuit devices.

The processes for making these (ceramic, metal or semiconductor) features generally involve providing a material layer or section of the substrate to be patterned, applying a layer of resist over the material layer or section, patternwise exposing the resist to radiation, developing the pattern by contacting the exposed resist with a solvent, etching the layer(s) underlying the resist layer at spaces in the pattern whereby a patterned material layer or substrate section is formed, and removing any remaining resist from the substrate. In some instances, a hard mask may be used below the resist layer to facilitate transfer of the pattern to a further underlying material layer or section. Examples of such processes are disclosed in U.S. Pat. Nos. 4,855,017; 5,362,663; 5,429,710; 5,562,801; 5,618,751; 5,744,376; 5,801,094; and 5,821,169, the disclosures of which patents are incorporated herein by reference. Other examples of pattern transfer processes are described in Chapters 12 and 13 of "Semiconductor Lithography, Principles, Practices, and Materials" by Wayne Moreau, Plenum Press, (1988), the disclosure of which is incorporated herein by reference. It should be understood that the invention is not limited to any specific lithography technique or device structure.

The following examples are given to illustrate the scope and spirit of the present invention. Because these examples are given for illustrative purposes only, the invention embodied therein should not be limited thereto.

EXAMPLE 1
Synthesis of Dimethyl (2-thienyl) Sulfonium Perfluorobutane Sulfonate

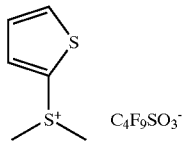

To a mixture containing 1.07 g (0.0082 mol) of 2-(methylthio)thiophene and 3.55 g (0.0246 mol) of methyl iodide in 20 ml of nitromethane, a solution of 3.34 g (0.0082 mol) of silver perfluorobutane sulfonate in 50 ml of nitromethane was added dropwise at room temperature. The resulting mixture was stirred at room temperature for about 15 hours. The reaction mixture was filtered through Celite to remove any white precipitate therefrom. The filtrate was concentrated to about 10 ml and then precipitated into 120 ml of diethyl ether. The white solid was collected by vacuum filtration and was further purified by recrystallization from hexane/ethyl acetate. The final yield is 2.83 g (78%). The product was identified as dimethyl (2-thienyl) sulfonium perfluorobutane sulfonate by NMR spectroscopy. Melting point: 75° C.

EXAMPLE 2
Absorbance of a Thiophene-containing Photo Acid Generator (PAG)

5.25 g of a cyclic olefin-maleic anhydride copolymer was dissolved in 34.4 g of propylene glycol monomethyl ether acetate (PGMEA). The solution was divided into two equal parts. To one part, 0.052 g (0.00012 mol) of dimethyl (2-thienyl) sulfonium perfluorobutane sulfonate was added. After the PAG was totally dissolved, both solutions were filtered through 0.2 μm pore size filter. The resulting filtrates were spin-coated onto quartz substrates and baked on a hot plate at about 130° C. for about 60 seconds. The absorbance of both films at 193 nm was then measured using a Cary 400 Bio UV-Visible Spectrophotometer. The difference in absorbance between the two films was measured to be 0.03 $\mu m^{-1}$, which is the contribution from the dimethyl (2-thienyl) sulfonium perfluorobutane sulfonate (0.0045 mol % vs. polymer).

For comparison, the absorbance of dimethyl (4-tolyl) sulfonium perfluorobutane sulfonate was measured in the same way. With the same concentration (0.0045 mol % vs. polymer), the absorbance of dimethyl (4-tolyl) sulfonium perfluorobutane sulfonate was measured to be 0.16 $\mu m^{-1}$, which is more than five times higher than that of dimethyl (2-thienyl) sulfonium perfluorobutane sulfonate.

EXAMPLE 3
Lithographic Evaluation

For the purpose of lithographic experiments, a photoresist formulation containing the dimethyl (2-thienyl) sulfonium perfluorobutane sulfonate PAG was prepared by combining the materials set forth below, expressed in part by weight.

| | |
|---|---|
| Propylene glycol monomethyl ether acetate | 87.34 |
| Poly(1-methylcyclopentyl-5-norbornene-2-carboxylate-co-5-norbornene-2-spirolactone-co-5-norbornene-2-carboxylic acid) | 11 |
| Dimethyl (2-thienyl) sulfonium perfluorobutane sulfonate | 0.33 |
| 2,5-Bis(adamatane-1-carboxyloxy)-2,5-dimethylhexane | 1.32 |
| Tetrabutylammonium hydroxide | 0.011 |

The photoresist formulation was spin-coated (for 30 seconds) onto an antireflective material (AR19, Shipley Company) layer applied on silicon wafers. The photoresist layer was soft-baked at about 130° C. for about 60 seconds on a vacuum hot plate to produce a film of about 0.4 μm thickness. The wafers were then exposed to 193 nm radiation (Nikon stepper, 0.6 NA). The exposure pattern was an array of contact holes. The exposed wafers were post-exposure baked on a vacuum hot plate at 130° C. for 90 seconds. The wafers were then (puddle) developed using 0.263 N tetramethyl ammonium hydroxide developer. The patterns were examined by scanning electron microscopy (SEM). Contact holes of 180 nm (325 nm pitch) were resolved.

While this invention has been particularly shown and described with respect to preferred embodiments thereof, it will be understood by those skilled in the art that the foregoing and other changes in forms and details may be made without departing from the spirit and scope of the present invention. It is therefore intended that the present invention is not limited to the exact forms and details described and illustrated, but fall within the scope of the appended claims.

Having thus described our invention in detail, what we claim as new and desire to secure by the Letters Patent is:

1. A chemically amplified resist composition comprising:
   (a) at least one chemically amplified base polymer comprising a fluorine-containing polymer or a silicon-containing polymer;
   (b) at least one photo acid generator, wherein said at least one photo acid generator is a thiophene-containing compound having the following formula:

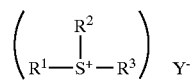

wherein at least one of $R^1$, $R^2$ or $R^3$ is thiophene or thiophene that is substituted with alkyl, alkoxy, or cycloalkyl, and the remaining $R^1$, $R^2$ or $R^3$, not containing a thiophene moiety, are independently selected from the group consisting of alkyl, cycloalkyl and aryl, or at least one of $R^1$, $R^2$ or $R^3$ are joined together to form a cyclic moiety having from about 4 to about 8 ring carbon atoms: and Y is a counter ion; and (c) a solvent for dissolving said at least one chemically amplified base polymer.

2. The chemically amplified resist composition of claim 1 wherein said at least one chemically amplified base polymer is an acid sensitive polymer which contains acid sensitive side chains that are capable of being cleaved by an acid generated by said at least one photo acid generator.

3. The chemically amplified resist composition of claim 2 wherein said acid sensitive polymer is a positive-tone polymer or a negative-tone polymer.

4. The chemically amplified resist composition of claim 1 wherein Y is a halogen, perfluorinated alkyl sulfonate, perfluorinated aryl sulfonate, perfluorinated alkyl sulfonyl methide, perfluorinated alkyl sulfonyl imide, perfluorinated aryl sulfonyl methide or perfluorinated aryl sulfonyl imide.

5. The chemically amplified resist composition of claim 1 wherein said thiophene-containing compound is selected from the group consisting of dimethyl (2-thienyl) sulfonium perfluorinated alkyl sulfonate, diphenyl-2-thienyl sulfonium perfluorinated alkyl sulfonate and 2-thienyl-tetrahydrothiophenium perfluorinated alkyl sulfonate.

6. The chemically amplified resist composition of claim 1 wherein said thiophene-containing compound is dimethyl (2-thienyl) sulfonium perfluorinated alkyl sulfonate.

7. The chemically amplified resist composition of claim 1 wherein said solvent is an ether, a glycol ether, an aromatic hydrocarbon, a ketene, an ester or mixtures thereof.

8. The chemically amplified resist composition of claim 7 wherein said solvent is a glycol ether.

9. The chemically amplified resist composition of claim 8 wherein said glycol ether is propylene glycol monomethylether acetate.

10. The chemically amplified resist composition of claim 1 further comprising a component selected from the group consisting of (i) at least one photosensitizer, (ii) at least one base, (iii) at least one dissolution modifying agent, (iv) at least one surfactant and any combinations of (i)–(iv).

11. The chemically amplified resist composition of claim 10 wherein said at least one photosensitizer is a chromophore selected from the group consisting of 9-anthracene methanol and 9,10-bis(trimethoxysily ethynyl)anthracene.

12. The chemically amplified resist composition of claim 10 wherein said at least one base is selected from the group consisting of berberine, cetyltrimethylammonium hydroxide, 1,8-bis(dimethylamino)naphthalene, tetrabutyl ammonium hydroxide, amines and polymeric amines.

13. The chemically amplified resist composition of claim 10 wherein said at least one surfactant is a fluorine-containing surfactant or a sioxane-containing surfactant.

14. The chemically amplified resist composition of claim 10 wherein said at least one dissolution modifying agent is selected from the group consisting of saturated steroid compounds, non-steroidal alicyclic compounds and non-steroidal multi-alicyclic compounds having plural acid-labile connecting groups between at least two alicyclic moieties.

15. The chemically amplified resist composition of claim 10 wherein from about 0.001 to about 8 weight % of said at least one photosensitizer, based on the total weight of the base polymer, is employed.

16. The chemically amplified resist composition of claim 10 wherein from about 0.1 to about 1.0 weight % of said at least one base, based on the total weight of the base polymer, is employed.

17. The chemically amplified resist composition of claim 10 wherein from about 0.001 to about 0.1 weight % of said at least one surfactant, based on the total weight of the base polymer, is employed.

18. The chemically amplified resist composition of claim 10 wherein from about 5 to about 25 weight % of said at least one dissolution modifying agent, based on the total weight of the base polymer, is employed.

19. The chemically amplified resist composition of claim 11 wherein from about 50 to about 30 weight % of said at least one chemically amplified base polymer, from about 50 to about 90 weight % of said solvent, and from about 0.5 to about 10 weight % of said at least one photo acid generator, said amount of said at least one photo acid generator is based on the total weight of the base polymer, are present in said composition.

20. The chemically amplified resist composition of claim 19 wherein from about 10 to about 20 weight % of said at least one chemically amplified base polymer, from about 80 to about 90 weight % of said solvent, and from about 1 to about 5 weight % of said at least one photo acid generator, said amount of said at least one photo acid generator is based on the total weight of the base polymer, are present in said composition.

21. A chemically amplified resist composition comprising:

(a) at least one chemically amplified base polymer;

(b) at least one photo acid generator, wherein said at least one photo acid generator is dimethyl (2-thienyl) sulfonium perfluorinated alkyl sulfonate, diphenyl-2-thienyl sulfonium perfluorinated alkyl sulfonate or 2-thienyl-tetrahydrothiophenium perfluorinated alkyl sulfonate; and (c) a solvent for dissolving said at least one chemically amplified base polymer.

22. The chemically amplified resist composition of claim 21 wherein said at least one chemically amplified base polymer is a phenolic-containing resin.

23. The chemically amplified resist composition of claim 22 wherein said phenolic-containing resin is a poly (hydroxystyrene) polymer.

24. The chemically amplified resist composition of claim 21 wherein said at least one chemically amplified base polymer is poly(meth)acrylate, a copolymer of a cyclic olefin and maleic anhydride, a cyclic olefin addition polymer, a cyclic-olefin-maleic anhydride-(meth)acrylate hybrid polymer or a cyclic olefin-(meth)acrylate polymer.

25. The chemically amplified resist composition of claim 21 wherein said at least one chemically amplified base polymer is a phenol formaldehyde, an acrylamide or a hydroxyimide group type polymer.

26. A method of forming a patterned material structure on a substrate, said material being selected from the group consisting of semiconductors, ceramics and metals, said method comprising:

(a) providing a substrate with a layer of said material, (b) applying a chemically amplified resist composition to said substrate to form a resist layer on said substrate, said resist composition comprising (a) a chemically amplified base polymer comprising a fluorine-containing polymer or a silicon-containing polymer, and (b) a photo acid generator, said acid generator comprising a thiophene-containing compound having the following formula:

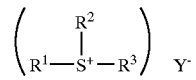

wherein at least one of $R^1$, $R^2$ or $R^3$ is thiophene or thiophene that is substituted with alkyl, alkoxy, or cycloalkyl, and the remaining $R^1$, $R^2$ or $R^3$, not containing a thiophene moiety, are independently selected from the group consisting of alkyl, cycloalkyl, and aryl, or at least one of $R^1$, $R^2$ or $R^3$ are joined together to form a cyclic moiety having from about 4 to about 8 ring carbon atoms; and Y is a counter ion;

(c) patternwise exposing said substrate to radiation whereby acid is generated by said acid generator in exposed regions of said resist layer by said radiation, (d) contacting said substrate with an aqueous alkaline developer solution, whereby portions of said resist layer are selectively dissolved by said developer solution to reveal a patterned resist structure, and (e) transferring resist structure pattern to said material layer, by etching into said material layer through spaces in said resist structure pattern.

\* \* \* \* \*